Figure 2:
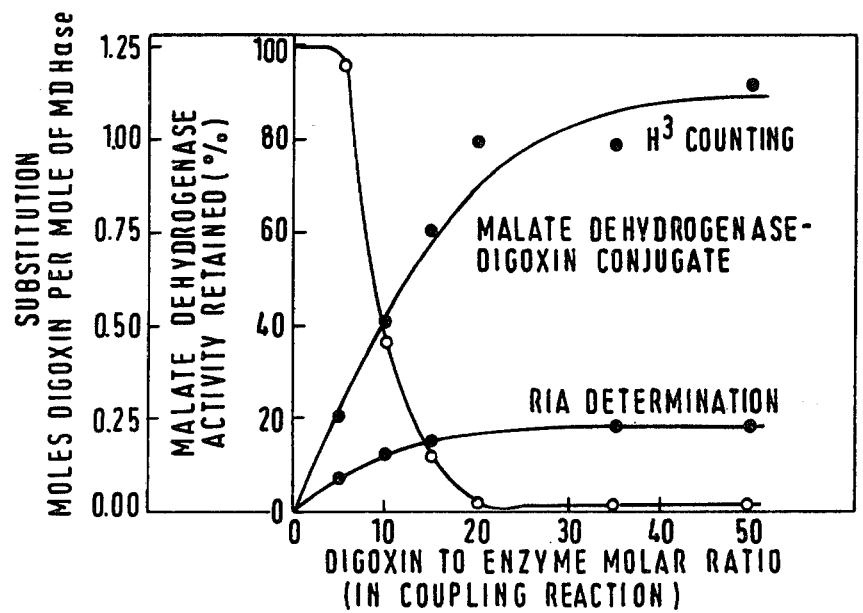

United States Patent [19]

Parikh et al.

[11] 4,298,685
[45] Nov. 3, 1981

[54] DIAGNOSTIC REAGENT

[75] Inventors: Indu Parikh; Pedro Cuatrecasas, both of Chapel Hill, N.C.

[73] Assignee: Burroughs Wellcome Co., Research Triangle Park, N.C.

[21] Appl. No.: 35,619

[22] Filed: May 3, 1979

[30] Foreign Application Priority Data

May 4, 1978 [GB] United Kingdom ............... 17749/78

[51] Int. Cl.$^3$ ........................ C12N 9/96; G01N 33/54
[52] U.S. Cl. ........................................ 435/7; 435/188; 435/810; 23/230 B; 424/12
[58] Field of Search .................. 23/230 B; 435/7, 188, 435/177, 810, 805; 424/1, 1.5, 12, 85, 88; 260/112 R, 121

[56] References Cited

U.S. PATENT DOCUMENTS 3,839,153 10/1974 Schuurs et al. ..................... 435/188
3,852,157 12/1974 Rubenstein et al. ................ 435/188
4,017,597 4/1977 Reynolds ................................. 435/7
4,134,792 1/1979 Boguslaski et al. ...................... 435/7

OTHER PUBLICATIONS

May et al. "NEO29-(t)-Biotinyl insulin and its Complexes with Avidin", *J. Biol. Chem.*, vol. 253, No. 3 (1978) pp. 686-690.
Manning et al. "A Method for Gene Enrichment Based on the Avidin-Biohn Interaction Application to the Drosophilia Ribosoma RNA Genes", *Biochem.*, vol. 16 No. 7 (1977) pp. 1364-1370.
Heggeness et al. "Use of the Avidin-Biotin Complex for the Localization of Actin and Myosin with Fluorescence Microscopy", *J. Cell Biol.*, vol. 73 (1977) pp. 783-788.
Hofmann et al. "Avidin-Biotin Affinity Columns, General Methods for Attaching Biotin to Peptides and Proteins", *J. Am. Chem. Soc.*, vol. 100, No. 11 (1978) pp. 3585-3590.
Bayer, et al. "Preparation of Ferriton-Avidin Conjugates by Reductive Alkylation for Use in Electron Microscopic Cytochemistry", *J. Hist. Cytochem.*, vol. 24, No. 8 (1976) pp. 933-939.

*Primary Examiner*—Thomas G. Wiseman
*Attorney, Agent, or Firm*—Donald Brown

[57] ABSTRACT

A sample, e.g. serum, containing an antigen, hapten or other biological substance is mixed with antibodies raised against that substance which have been tagged with biotin, and with a known amount of that substance labelled with an enzyme. After the competitive complexation of the antibody with the labelled substance and the substance to be detected, avidin, immobilised on an inert support is added. The avidin binds to the biotin and causes the complex to be precipitated. The solid and liquid phases are separated by centrifugation and the amount of biological substance in the original sample is determined by measuring the activity of the enzyme in either phase.

18 Claims, 5 Drawing Figures

A GENERAL SCHEME OF THE ASSAY TECHNIQUE

1. ADDITION OF REAGENTS
   A. PATIENT, CONTROL SERA
   B. ENZYME-LABELED DIGOXIN
   C. IMMOBILIZED AVIDIN
   D. BIOTINIZED ANTIBODY

2. INCUBATION — 60-90 MIN., SHAKING, ROOM TEMP.

SUSPEND IN 5ML ICE-COLD BUFFER

3. WASHING — CENTRIFUGE, ASPIRATE SUPERNATE AWAY

SOLID PHASE (GEL PELLET)

4. ENZYMATIC ASSAY — ADD ASSAY BUFFER SHAKE 1 HR., ROOM TEMP.

SPECTROPHOTOMETRIC DETERMINATION OF ENZYMATIC ACTIVITY

FIG. 1

DIAGNOSTIC REAGENT

The present invention provides a quantitative method for the determination of biological substances and more particularly, provides an enzyme immunoassay of such substances in biological fluids.

There is a continuous need in medical practice and research for rapid, accurate, quantitative determinations of biological substances at extremely low concentrations. The presence of drugs or narcotics in body fluids, such as saliva, blood or urine, has to be determined in very small quantities with satisfactory accuracy. In addition, in medical diagnosis, it is frequently important to know the presence of various substances which are synthesised naturally by the body or ingested. These include hormones, both steroids and polypeptides, prostaglandins, and toxins as well as other materials which may be involved in body functions.

To meet these needs, a number of ways have been devised for analysing for trace amounts of materials. A common method for isolating and detecting substances in biological fluid is use of thin layer chromatography (TLC), for example, in combination with mass spectroscopy or gas phase chromatography. However, TLC has a number of deficiencies in being slow, being subject to a wide range of interfering materials, and suffering from severe fluctuations in reliability. Therefore, the absence of satisfactory alternatives has resulted in intense research efforts to determine improved methods of separation and identification.

An alternative to TLC has been radioimmunoassay (RIA). Here antibodies for specific haptens or antigens are employed. By mixing an antibody with solutions of the hapten or antigen, and with a radioactive hapten or antigen analogue, the radioactive analogue will be prevented from binding to the antibody to an extent directly related to the concentration of hapten or anitgen in the solution. By then separating and assaying the free radioactive analogue from the antibody bound radioactive analogue, one can indirectly determine the amount of hapten or antigen in the original solution. However, the use of radioisotopes in such an assay could be a potential health hazard and, furthermore, the instrumentation generally required for radioimmunoassay is relatively sophisticated and generally too expensive too allow small hospitals and physicians to routinely perform, for example, a patient's blood or urine analysis. Enzyme immunoassay overcomes the above problems and in addition, has the unique advantage of potential amplification of the measured parameter.

In essence this method replaces the radioactive biological substance analogue with an enzyme labelled biological substance (hapten or antigen). Such modified enzyme molecules retain their enzymatic activity and the enzyme-labelled biological substance will compete for antibody complex formation with the unknown amount of free biological substance in the system. The complexes may be separated (cf. U.K. Pat. No. 1,348,935) in view of their insolubility in certain instances and the activity of this, or the part remaining in solution is used as a measure of the amount of antigen originally present. The same principle may be applicable to a reverse system, using enzyme-labelled antibodies whenever the unmodified version of the same antibody present in biological fluids has to be determined.

It has now been found that covalent attachment of biotin (Vitamin H) to the antibody molecule, resulting in a soluble biotin-tagged complex, facilitates convenient separation of all antibody forms including all enzyme-labelled and unlabelled biological substance-antibody complexes. The separation process can then be performed by the use of the biotin-specific receptor protein, avidin, which is immobilised in an insoluble form. The very strong affinity between avidin and biotin, which approaches covalent bond character, results in insolubilisation of all antibody forms and consequently allows an extremely efficient and easy removal of all biotin-tagged antibodies, and complexes formed by such antibodies.

According to one aspect of the present invention, therefore, there is provided a process for the detection and/or determination of a biological substance in a test sample, which comprises admixing the test sample, a predetermined quantity of a soluble enzyme-labelled form of the biological substance, and a predetermined quantity of a soluble biotintagged antibody raised against the biological substance, allowing to come to equilibrium, adding insolubilised avidin, separating the resulting solid phase from the liquid phase and determining the enzyme activity of either of these phases.

For the purposes of the present invention, any biological substance may be detected and/or determined for which an appropriate antibody may be produced having satisfactory specificity and affinity for the biological substance. The recent literature contains an increasing number of reports of antibodies for an increasingly wide variety of biological substances. Compounds for which antibodies can be provided range from simple phenylaklyl amines, for example amphentamine, to very high molecular weight polymers, for example proteins.

The biological substances for detection and/or determination in the process of the present invention may be divided into three different categories, based on their biological relationship to the antibody. The first category is antigens, which when introduced into the blood stream of a vertebrate, result in the formation of antibodies. The second category is haptens, which when bound to an antigenic carrier, and the hapten-bound antigenic carrier is introduced into the bloodstream of a vertebrate, elicit formation of antibodies specific for the hapten. The third category of biological substances includes those which have naturally occurring antibodies in a living organism and the antibodies can be isolated in a form specific for the biological substance.

The most important group of biological substances for the purposes of the present invention are those of the second category, the haptens. Methods for the production of antibodies to the three different categories of biological substances are well known in the art.

Selection of the enzyme for use in the present invention is governed by a number of criteria. Thus it should possess potentially reactive groups to which the biological substance can be coupled without destroying enzyme activity and should not occur naturally to an appreciable extent in the type of tissue to be assayed for the said biological substance. In addition, the enzyme should have a relatively long shelf life, a high specific activity and also be capable of being easily assayed, for example with a visible light spectrophotometer.

Examples of enzymes which may conveniently be employed in the process of the present invention are, malate dehydrogenase, staphylococcal nuclease, delta-5-ketosteroid isomerase, yeast alcohol dehydrogenase, yeast glucose-6-phosphate dehydrogenase, alpha glycerophosphate dehydrogenase, triose phosphate isomerase, and horse radish peroxidase, more preferably, alkaline phosphatase, asparaginase, glucose oxidase, beta-galactosidase and ribonuclease. Normally it is preferred to purify the enzyme, for example by dialysis against saline, before use.

The preparation of the enzyme-labelled biological substances for use in the present invention can take place in various ways known per se in the art. Some biological substances may already possess groups that can be cross-linked with reactive groups at the surface of the enzyme, while other substances will have to be provided with such groups by organic chemical reactions. It should be emphasised that neither the original immunological properties of the biological substance nor the activity of the enzyme ought to change appreciably during this process. The groups of the enzyme which are particularly suited for coupling reactions are amino and carboxyl groups. If the modified or unmodified biological substance also possesses such groups, the coupling can be performed by, for example, reactions known from peptide synthesis. Furthermore, such substances, as for example, glutaraldehyde, difluorodinitrodiphenylsulphone, toluene diisocyanate, di- and trichloro-s-triazine and others can be employed for the coupling reaction.

Examples of the coupling of biological substances to enzymes are described in, for example, L. A. Steinberger, Immunocytochemistry, Prentice Hall, New Jersey (1974).

Specific examples of the coupling of haptens to proteins are described in, for example, C. A. Williams and N. W. Chase, Methods of Immunology and Immunochemistry Vol. 1 Academic Press, New York, 1967. The methods described are used for the preparation of conjugates for immunisation but they can also be used for the preparation of the enzyme-labelled biological substances which are essential in the process of the present invention.

Biotin-tagged antibody is conveniently prepared by reaction of a biotin derivative, for instance a biotin ester derivative such as the N-hydroxysuccinimide ester of biotin, with the antibody. The biotin ester derivative is dissolved in a polar, aprotic solvent, for example dimethylformamide, and is then added in a 20 to 300 molar excess to the antibody in 0.01 M to 1.0 M, preferably 0.05 M to 0.5 M, most preferably 0.1 M phosphate buffer, for example potassium phosphate buffer at from pH 6.5 to pH 8.5, preferably pH 7.5. After admixture of the reactants, the reaction is allowed to proceed at a temperature of from 2° to 10° C., more preferably at 4° C. for a time sufficient for its completion. Normally this takes of the order of 10 hours. After completion of the reaction, the biotin-tagged antibody may be separated from the reaction mixture by standard methods well known in the art, for example by gel permeation chromatography on, for instance, a cross-linked dextran.

Insolubilised avidin, that is, avidin immobilised by attachment to a solid support, may be prepared by a method in actual use or described in the literature, for example, by covalent binding with macromolecular insoluble carriers such as agarose, polystyrene, polyacrylamide, nylon, cross-linked dextran or filter paper or by physical coupling to insoluble carriers such as glass beads or plastic objects, or to the inside of test tubes made from either plastic or glass or to microtitre plates.

Specific examples of coupling haptens and other biological molecules to agarose and polyacrylamides are described by Cuatrecasas in *J. Biol. Chem.*, 245, 3059–3065, (1970). W. B. Jacoby and M. Wilcheck; *Methods in Enzymology;* Vol. 34—Academic Press, New York 1974. These methods may also be used, in principle, to prepare (a) avidin-solid support, (b) hapten-protein conjugates and (c) biotin-antibody conjugates. Conveniently either avidin or the carrier is activated before covalent binding occurs, but most conveniently the carrier is activated before covalent binding. In one form of the invention the carrier used is agarose since this exhibits excellent coupling of avidin and retention of biotinbinding capacity. Most preferably, benzoquinone-activated agarose is used due to its ease of preparation, and its lack of non-specific absorption of enzyme. In other forms of this invention avidin is coupled to nylon rings or rods or to the inside of polystyrene test-tubes.

A schematic representation of the assay is presented in FIG. 1. To the vessel in which the reaction is to take place are added at room temperature and at near physiological pH, preferably at pH 7, successively, with a minimum time interval between the additions: free biological substances for example, contained in a serum sample, an aqueous solution of enzymelabelled biological substance, and a quantity of previously tagged antibody sufficient to neutralise (ie. complex with) 50%–80% of the enzyme-labelled biological substance. These three components are mixed, and immediately insolubilised avidin is added to the reaction mixture to create a heterogeneous system and the mixture shaken until a predetermined equilibrium point is reached. The quantity of avidin used is normally several hundred fold in excess of that theoretically required. The solid phase removes the free antibody as well as the antibody bound to the biological substance. The supernatant contains enzyme-labelled biological substance in direct proportion to the level of free biological substance, whilst the deposited solid phase has enzyme-labelled biological substance in inverse proportion to level of the free biological substance. Either the deposited solid phase or the supernatant can then be assayed for enzymatic activity to determine the amount of biological substance present in the unknown sample.

The enzyme activity measurement of the solid and/or liquid phase of the reaction mixture resulting from the process of the present invention may be carried out by methods already known in themselves. See, for example, H. U. Bergmeyer, Method for Enzymatic Analysis, Academic Press, New York (1965). The assay of the carefully separated and rinsed solid phase may take place after removal of the supernatant by, for example, aspiration.

The various forms in which the reagents of the present invention can be used are manifold. For instance, the enzyme labelled biological substance can be freeze-dried or dissolved in a buffer. Furthermore, a solid carrier for example, a strip of paper impregnated with the enzyme-labelled biological substance, can be employed.

For carrying out the process for a single test according to the present invention, use can be made of a pack comprising, in separate containers:

(a) a preselected quantity of enzyme-labelled biological substance;

(b) a preselected quantity of biotin-tagged antibody raised against the said biological substance;

(c) a preselected quantity of insolubilised avidin; and (d) a substrate or substrates and co-factors for the determination of the activity of the enzyme employed, together with instructions to admix the enzyme-labelled biological substance, the biotin-tagged antibody raised against the biological substance, and a test sample, allowing the mixture to come to equilibrium, then adding the insolubilised avidin, separating the resulting solid phase form the liquid, and determining the enzyme activity of either of these phases using the enzyme substrate or substrates and co-factors.

If required, it may also contain the necessary auxiliaries for making a dilution series of the test sample to be examined for a quantitative determination, such as test tubes, pipettes and flasks of diluent.

The invention is illustrated further by the following examples which are not to be construed as limiting the invention to the specific procedures described in them.

EXAMPLE 1

Coupling of digoxin to enzymes

Digoxin was coupled to enzyme in the following manner:

$^3$H-digoxin (250 $\mu$Ci/mg) in ethanol was reacted with a slight molar excess of sodium metaperiodate for two hours. An aliquot of oxidised $^3$H-digoxin (50 nmoles) was added to enzyme (5 nmoles) in sodium acetate buffer (1 ml; 200 mM; pH 7). The final concentration of ethanol was usually 10–20%. Sodium cyanoborohydride (10–20 mg) was added and the reaction was allowed to proceed for 3 days at 4° C. Labelled enzyme was separated from the reactants by gel exclusion chromatography on Sephadex G-50. The table below shows the degree of substitution by digoxin (calculated by means of radioactivity measurements) and the retention of enzymatic activity for four enzymes after reaction under the described conditions.

| Enzyme | Digoxin substitution (M/M) | | Specific activity recovered as % of control |
|---|---|---|---|
| | $^3$H counting | RIA | |
| Malate dehydrogenase | 0.50 | 0.10 | 36.7 |
| Alkaline Phosphatase | 1.10 | 0.15 | 92.3 |
| Glucose Oxidase | 1.70 | 0.30 | 100.0 |
| Asparaginase | 1.00 | 0.60 | 100.0 |

Conjugation of $^3$H-digoxin with malate dehyrdogenase was investigated more fully (FIG. 2). Oxidised digoxin was reacted at various concentrations (molar excess varied from 5 to 50) with aliquots of enzyme, and the retention of enzyme specific activity was determined for each point. In addition, the degree of substitution of digoxin was determined both by tritium counting to determine the absolute number of haptens and by RIA to determine the number of immunologically reactive digoxin residues. The data shows that malate dehydrogenase is very sensitive to the degree of labelling by digoxin and that only 20% of the groups attached are functionally available to interact with antibody.

Insolubilisation of Avidin

Avidin was coupled directly to a solid support of benzoquinone-activated sepharose. The avidin-gel was diluted, as desired, with underivatised sepharose.

A 50% suspension of agarose in sodium phosphate buffer (100 mM; pH 8.0) was added in a 4:1 volume/volume ratio to p-benzoquinone (250 mM) in ethanol. After stirring the suspension for 1 hour at room temperature, the activated gel was washed by suction filtration using equal volumes of, successively, ethanol (20%), aqueous sodium chloride (1.0 M), water, and sodium phosphate (pH8, 100 mM). The gel (1 volume) was then added to avidin (1 volume; 10 mg/ml) dissolved in sodium phosphate buffer (pH8, 100 mM), and the resulting suspension was shaken for 15 hours at 4° C. After this time, the avidin-gel conjugate was washed successively with 5 volumes each of sodium acetate (0.1 M, pH 4.0) containing sodium chloride (500 mM), sodium bicarbonate (0.1 M, pH 9.0) containing sodium chloride (500 mM), and water. The substitution of avidin on the gel was in the range of 4–5 mg/ml packed gel. The substituted avidin was found to have 100% of its biotin binding capacity.

Substitution of Antibody with biotin

Sheep antidigoxin antibody was treated variously in potassium phosphate (0.1 M; pH 7.5) with a 20 to 300 molar excess of the N-hydroxysuccinimide ester of biotin in dimethylformamide (DMF). The final concentration of DMF was 50%. After incubation overnight at 4° C., the biotinised antibody was separated from reactants by gel permeation chromatography on Sephadex G-50. The titre of the biotinised antibody was assessed using $^{125}$I-digoxin and dextran-coated charcoal. The sensitivity of the biotinised antibody to avidin-gel was assessed using previously iodinated antibody and measuring the take-down of $^{125}$I by avidin-gel. At levels of biotinisation above 3 biotin molecules per antibody molecule, the antibody retained its titre for digoxin and was completely absorbed by avidin-gel. The antibody-biotin preparation chosen for the enzyme immunoassay empirically met these criteria.

Figure 3:
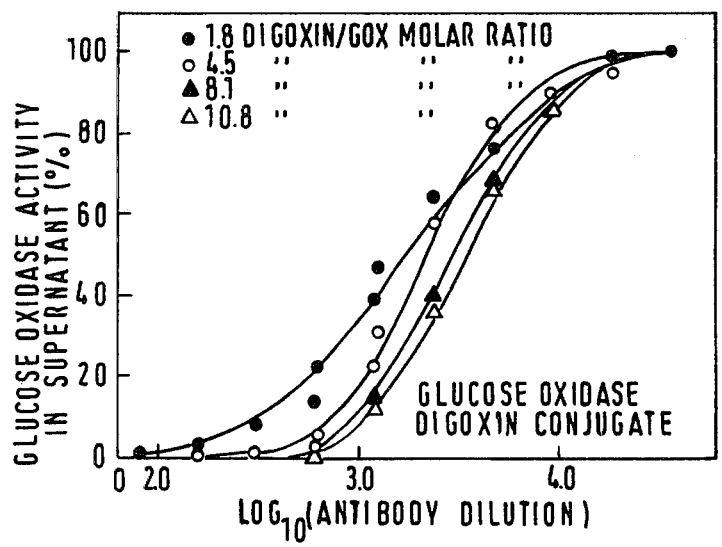

Glucose oxidase-digoxin conjugates, with various levels of substitution of digoxin, were titrated with various dilutions of biotinised antibody and excess avidin-gel (FIG. 3). The enzyme derivatives has been previously shown not to be inhibited by even very high concentrations of anti-digoxin antibody. The data shows that at between 1:100 and 1:1000 dilution of the stock antibody solution, the digoxin-enzyme and antibody are at approximately stoichiometric levels such that essentially all enzyme activity is precipitated by the gel. The data also shows that with increasing digoxin substitution less antibody is needed to precipitate 50% of the enzyme activity, indicating that the immunoreactivity of the enzyme conjugate is increasing with substitution.

The anti-digoxin antibody and digoxin interaction

Using appropriate levels of glucose oxidase-digoxin, biotin-tagged antibody, and excess avidin-gel, the time course to reach equilibrium between the three components of the assay was followed. Glucose oxidase-digoxin and avidin-gel were preincubated at room temperature. At t=0, biotin-tagged antibody was added and the mixture was shaken at room temperature. At various time intervals, aliquots of the assay mixture were centrifuged and the supernatants assayed for enzyme activity. In general, maximum takedown of enzyme-labelled digoxin by the antibody-avidin gel complex occured within 90 minutes, while the binding of biotin-tagged antibody by avidin-gel is essentially complete within 10 minutes.

Enzyme Immunoassay for digoxin

Serum digoxin (50 $\mu$l), glucose oxidase-labelled digoxin (50 $\mu$l) which contained 1 ng/ml of bound digoxin, and appropriately diluted biotin-tagged antidigoxin antibody (50 μl) were mixed in a test tube (FIG. 1). Immediately a 50% aqueous suspension of avidin-sepharose (50 μl) which had been previously diluted 1:10 with native sepharose was added. All assay reagents were in phosphate buffer (50 mM; pH 7) containing bovin serum albumin (0.1%). The reaction mixture was then incubated for 2 hours at room temperature with shaking, and was subsequently suspended in ice-cold buffer (5 ml) containing bovin serum albumin (0.1%). The mixture was centrifuged and the supernatant aspirated away to leave the gel pellet. After washing the pellet, assay buffer (1.0 ml) containing glucose (100 mM), o-dianisidine (0.1 mg/ml) and horse radish peroxidase (7.5 μg/ml) in sodium phosphate buffer (100 mM; pH 6) was added, and shaking was performed for 1 hour. Alternatively, 0.1 mM; 2,2-azino-bis-(3-ethylbenzthiozoline sulphonic acid) (ABTS) can be substituted for the o-dianisidine as an enzyme substrate.

After this time the mixture was cooled, and the optical density of the supernatant was recorded at a wavelength of 450 nm and the values of the patient sera compared to a standard curve constructed with control sera.

Figure 4:
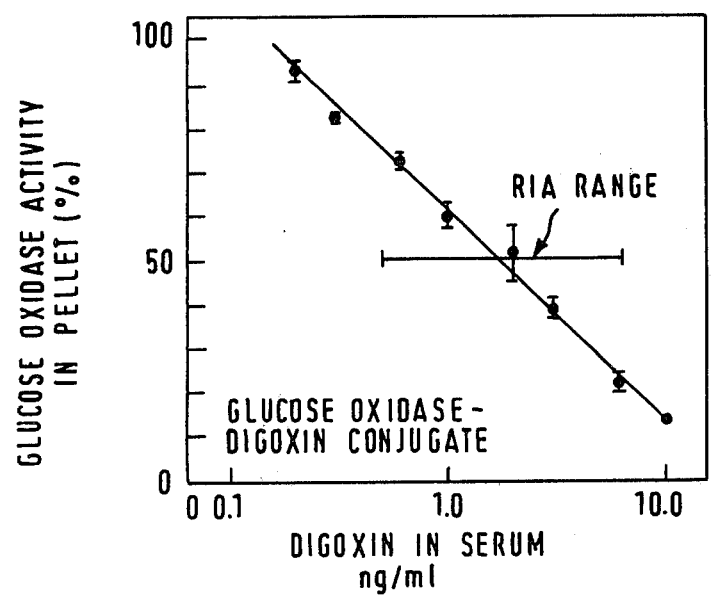

FIG. 4 shows the effect of addition of various amounts of free digoxin (plotted as the logarithm of the digoxin concentration in ng/ml versus the percentage of total enzyme activity on the gel) to the incubation mixture. The relationship between free digoxin levels and the enzyme activity is linear over 0.15 to 10.00 ng/ml of free digoxin.

EXAMPLE 2: Codeine

To illustrate the general applicability of the principle of the herein described enzyme immunoassay, the narcotic drug codeine was assayed by this method.

Coupling of Codeine to Glucose Oxidase

Codeine hemisuccinate (20 μmoles) dissolved in dry, redistilled dimethylformamide (600 μl) was added to 200 μmoles N-hydroxysuccinimide dissolved in dry, redistilled dioxane (300 μl) and 20 μmoles dicyclohexylcarbodiimide in dry, redistilled dioxane (30 μl). The mixture was allowed to react a room temperature for 5-6 hours in a tightly stoppered test tube. The codeine hemisuccinate N-hydroxysuccinimide thus prepared in situ was used without purification to couple to the enzyme. To 5 nmoles of enzyme (glucose oxidase) dissolved in 600-900 μl of sodium acetate buffer (100 mM, pH 7.0) was added 100-500 μl (preferably 300 μl) of the codeine N-hydroxysuccinimide ester solution as prepared and described above. After 12-24 hours at room temperature the enzyme (codeine conjugated together with any unconjugated enzyme) was separated from the reactants by gel exclusion chromatography. The degree of codeine substitution to glucose oxidase was determined by radioimmunoassay. As in the case of digoxin the degree of substitution of codeine varies depending on the reaction conditions. A substitution of 3-5 codeine molecules per enzyme (glucose oxidase) molecule was found to be ideal for the present assay method.

Coupling of biotin to anti-codeine antibody

This reaction was performed as described in Example 1 for coupling of biotin to anti-digoxin antibody. The titer of biotinized antibody was essentially unaltered as compared to the underivatized antibody. Antibody preparations with 3 or more convalently bound biotin molecules were completely precipitable by solid-phase avidin and were found to be ideally suited for the present assay.

Enzyme Immunoassay for Codeine

Figure 5:
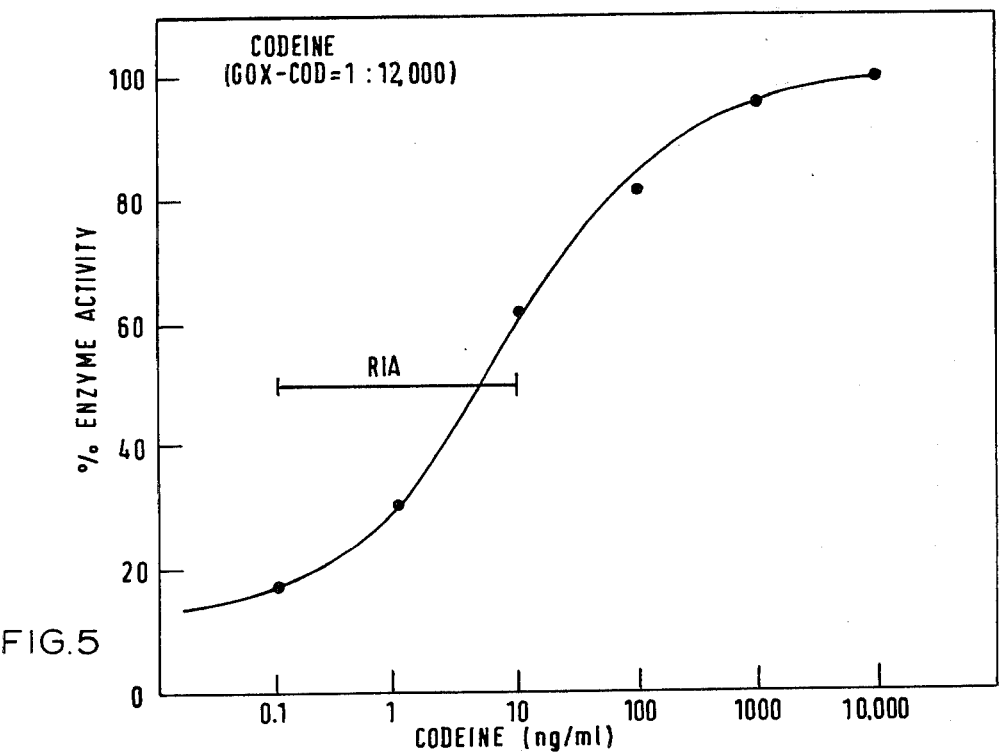

With appropriate, predetermined quantities of enzyme-codeine conjugate, biotinized anti-codeine antibody and solid-phase avidin the time course to reach equilibrium between the three components of the assay was determined. Usually after 45–60 minutes the system is at equilibrium. Codeine standard (0.1 to 10,000 ng/ml solutions (50 μl), glucose oxidase-codeine conjugate (50 μl, containing 1–20 fmoles codeine) and appropriately diluted biotin tagged anti-codeine antibody were mixed in a test tube. A 50% aqueous suspension of solid-phase avidin (50 μl) was added to the above mixture. All assay reagents were prepared in 50 mM phosphate buffer, pH 7 containing 0.1% bovine serum albumin. The reaction mixture after incubation for 2 hours at room temperature was diluted with 5 ml of ice-cold buffer containing 0.1% bovine serum albumin. The mixture was centrifuged and the supernatent aspirated away. After washing the pellet the assay buffer (1 ml) containing glucose (100 mM, o-dianisidine (0.1 mg/ml) and horse radish peroxidase (7–5 μg/ml) in phosphate buffer (100 mM, pH 6) was added. The assay mixture was incubated for 30–90 minutes (preferably 60 minutes) at room temperature, cooled in ice bath and optical density at 450 nm was recorded. Thus a standard curve with various codeine concentrations was constructed (FIG. 5).

We claim:

1. A process for the quantitative determination of a biological substance in a test sample comprising,
   (a) mixing said test sample, a soluble enzyme-labelled form of said biological substance, and a soluble biotin-tagged antibody raised against said biological substance,
   (b) incubating the mixture under conditions suitable for forming an antibody-biological substance complex,
   (c) then adding isolubilized avidin, separating the resulting solid phase from the liquid phase, and
   (d) determining the enzyme activity of either of said phases.

2. A process as claimed in claim 1 wherein said enzyme of said substance is selected from the group consisting of malate dehydrogenase, staphylococcal nuclease, delta-5-ketosteroid isomerase, yeast alcohol dehydrogenase, yeast glucose-6-phosphate dehydrogenase, alpha glycerophosphate dehydrogenase, triose phosphate, isomerase, horse radish peroxidase, alkaline phosphatase, asparaginase, glucose oxidase, beta-galactosidase and ribonuclease.

3. A process as claimed in claim 1 or 2 wherein the avidin is insolubilised by covalent binding to a macromolecular insoluble carrier.

4. A process as claimed in claim 3 wherein said macromolecular insoluble carrier is selected from the group consisting of agarose, polystyrene, polyacrylamide, nylon, cross-linked dextran and filter paper.

5. A process as claimed in claim 4 wherein said macromolecular insoluble carrier is agarose.

6. A process as claimed in claim 1 wherein the avidin is insolubilised by physical coupling to an insoluble carrier.

7. A process as claimed in claim 6 wherein said insoluble carrier is selected from the group consisting of glass beads, plastic objects, the inside of plastic test tubes, the inside of glass test tubes and microtitre plates.

8. A process as claimed in claim 1; wherein said biological substance is an antigen.

9. A process as claimed in claim 1 wherein said biological substance is a hapten.

10. A process as claimed in claim 1 wherein said biological substance is digoxin or codeine.

11. A kit for use in enzyme immunoassay comprising,
 (a) a quantity of enzyme-labelled biological substance,
 (b) a quantity of biotin-tagged antibody raised against said biological substance,
 (c) a quantity of insolubilized avidin, and
 (d) a quantity of substrate for said enzyme,
 wherein said quantity of biotin tagged antibody is sufficient to bind a substantial quantity of the enzyme-labelled substance, said quantity of insolubilized avidin is present in excess of the amount required to precipitate the biotin tagged antibody, and said quantity of said substrate is sufficient to react with said enzyme label to produce a detectable signal.

12. A kit as claimed in claim 11 wherein the enzyme is selected from the group consisting of malate dehydrogenase, staphylococcal nuclease, delta-5-ketosteroid isomerase, yeast alcohol dehydrogenase, yeast glucose-6-phosphate dehydrogenase, alpha glycerophosphate dehydrogenase, triose phosphate isomerase, horse radish peroxidase, alkaline phosphatase, asparaginase, glucose oxidase, beta-galactosidase and ribonuclease.

13. A kit as claimed in claim 11 wherein the avidin is insolubilised by covalent binding to a macromolecular insoluble carrier.

14. A kit as claimed in claim 13 wherein said macromolecular insoluble carrier is selected from the group consisting of agarose, polystyrene, polyacrylamide, nylon cross-linked dextran and filter-paper.

15. A kit as claimed in claim 14 characterised in that said macromolecular insoluble carrier is agarose.

16. A kit as claimed in claim 11 wherein the avidin is insolubilised by physical coupling to an insoluble carrier.

17. A kit as claimed in claim 16 wherein said insoluble carrier is selected from the group consisting of glass beads, plastic objects, the inside of a test tube made from plastic and the inside of a test tube made from glass.

18. A kit as claimed in any one of claims 11 to 17 wherein said biological substance is digoxin or codeine.

* * * * *